United States Patent
Silvo et al.

(10) Patent No.: US 9,995,714 B2
(45) Date of Patent: Jun. 12, 2018

(54) APPARATUS AND ARRANGEMENT FOR MONITORING A CONDITION OF AN ELONGATED FERROUS OBJECT HAVING A LONGITUDINAL AXIS

(71) Applicant: KONECRANES GLOBAL CORPORATION, Hyvinkää (FI)

(72) Inventors: Joni Silvo, Helsinki (FI); Antti Tanskanen, Oulu (FI)

(73) Assignee: KONECRANES GLOBAL CORPORATION, Hyvinkää (FI)

( * ) Notice: Subject to any disclaimer, the term of this patent is extended or adjusted under 35 U.S.C. 154(b) by 241 days.

(21) Appl. No.: 15/035,416

(22) PCT Filed: Nov. 11, 2014

(86) PCT No.: PCT/FI2014/050848
§ 371 (c)(1),
(2) Date: May 9, 2016

(87) PCT Pub. No.: WO2015/071538
PCT Pub. Date: May 21, 2015

(65) Prior Publication Data
US 2016/0290963 A1    Oct. 6, 2016

(30) Foreign Application Priority Data
Nov. 12, 2013    (FI) ...................... 20136108

(51) Int. Cl.
*G01N 27/82* (2006.01)
*G01N 27/83* (2006.01)
(Continued)

(52) U.S. Cl.
CPC ............. *G01N 27/82* (2013.01); *B61B 12/06* (2013.01); *B65G 43/02* (2013.01); *B66B 7/123* (2013.01);
(Continued)

(58) Field of Classification Search
CPC ........ G01N 27/72; G01N 27/82; G01N 27/83; G01N 29/04; G01N 2291/2626;
(Continued)

(56) References Cited

U.S. PATENT DOCUMENTS

| 4,449,408 A | 5/1984 | Brooks et al. |
| 5,320,103 A | 6/1994 | Rapoport et al. |
| 5,610,522 A | 3/1997 | Locatelli et al. |
| 6,492,808 B1 * | 12/2002 | Sukhorukov ............ G01B 7/32 324/235 |

(Continued)

FOREIGN PATENT DOCUMENTS

| DE | 33 46 774 A1 | 7/1985 |
| EP | 2 506 003 A1 | 10/2012 |

(Continued)

*Primary Examiner* — Arleen M Vazquez
*Assistant Examiner* — Steven Yeninas
(74) *Attorney, Agent, or Firm* — Birch, Stewart, Kolasch & Birch, LLP

(57) ABSTRACT

There is provided an apparatus for monitoring a condition of an elongated ferrous object having a longitudinal axis, said apparatus including at least one magnetizing circuit including magnetic poles separated along the longitudinal axis, and magnetic field sensors arranged at the poles, said poles including pole shoes for directing magnetic flux between the poles and the monitored object. The pole shoes include openings between the monitored object and the poles, an opening including two ends separated in a direction perpendicular to the longitudinal axis by a mid-section defining a smaller opening than the ends for concentrating the magnetic flux at the mid-section. There is further provided an arrangement including one or more elongated objects for hoisting payload, wherein the monitoring apparatus is attached to the elongated objects.

11 Claims, 2 Drawing Sheets

(51) Int. Cl.
  *B66B 7/12* (2006.01)
  *G01R 33/00* (2006.01)
  *B66C 15/06* (2006.01)
  *B61B 12/06* (2006.01)
  *B65G 43/02* (2006.01)
  *B66D 1/54* (2006.01)

(52) U.S. Cl.
  CPC ............... *B66C 15/06* (2013.01); *B66D 1/54* (2013.01); *G01N 27/83* (2013.01); *G01R 33/0011* (2013.01)

(58) Field of Classification Search
  CPC ......... B61B 12/06; B65G 43/02; B66B 7/123; B66C 15/06; B66D 1/54; G01R 33/0011
  USPC ........... 73/643; 324/225–230, 235, 237, 238, 324/240–243, 260–262
  See application file for complete search history.

(56) References Cited

U.S. PATENT DOCUMENTS

| | | | |
|---|---|---|---|
| RE40,166 E | | 3/2008 | Sukhorukov et al. |
| 2007/0090834 A1* | | 4/2007 | Osada ............ B66B 5/125 324/240 |
| 2010/0148766 A1* | | 6/2010 | Weischedel ........ G01N 27/9033 324/238 |
| 2011/0006762 A1* | | 1/2011 | Yoshioka ............... G01N 27/83 324/240 |
| 2013/0147471 A1* | | 6/2013 | Weischedel ............ G01N 27/83 324/238 |

FOREIGN PATENT DOCUMENTS

| | | |
|---|---|---|
| GB | 2 071 331 A | 9/1981 |
| JP | 2009-122074 A | 6/2009 |
| SU | 1430865 A1 | 10/1988 |

* cited by examiner

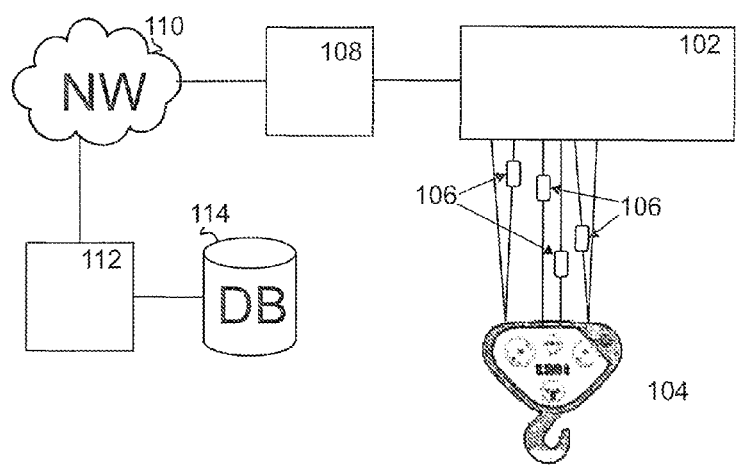
Figure 1
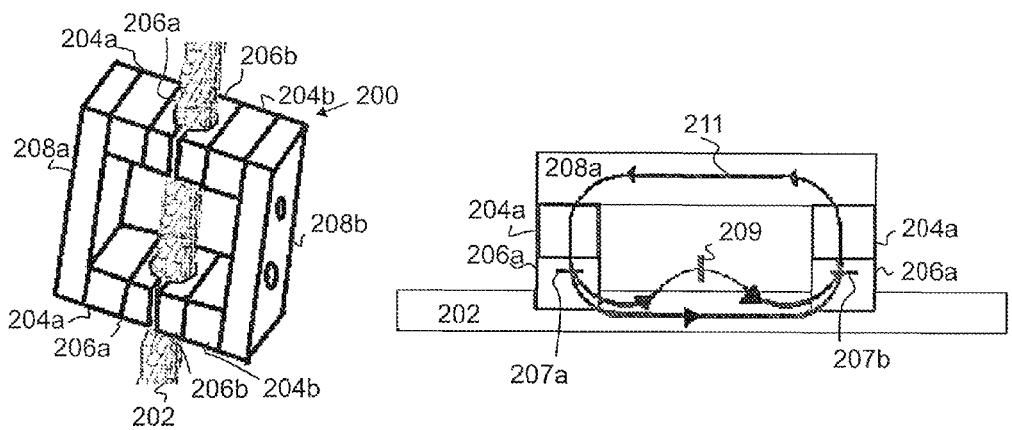
Figure 2a
Figure 2b

APPARATUS AND ARRANGEMENT FOR MONITORING A CONDITION OF AN ELONGATED FERROUS OBJECT HAVING A LONGITUDINAL AXIS

FIELD

The present invention relates to monitoring condition of elongated ferrous objects, for example ropes, and particularly to monitoring, where a magnetic flux is guided through the object being monitored.

BACKGROUND

The following description of background art may include insights, discoveries, understandings or disclosures, or associations together with disclosures not known to the relevant art prior to the present invention but provided by the invention. Some such contributions of the invention may be specifically pointed out below, whereas other such contributions of the invention will be apparent from their context.

Ropes are typically used in cranes for hoisting cargo, for example containers. Ropes wear during use and their condition needs to be monitored to ensure their safety. Typical faults of ropes include Local Faults (LFs), where single wires are broken on the surface of the rope or inside the rope, and Loss of Metallic Area (LMA), where the diameter of the rope is reduced. A faulty rope may have an increased diameter by the surface of the rope being faulty. The diameter may be increased for example by dirt, a foreign object being attached to the rope, and/or loose strands or wires on the surface of the rope. In another example the rope may be faulty by a foreign object being attached to the rope, whereby the diameter of the rope may be increased.

Typically condition of ropes is checked by measuring each rope at a time over its whole length to determine the condition. Dedicated measurement instruments may be attached to the rope for the duration of the measurement and the maintenance personnel performing the measurements may also inspect the rope visually. After the measurements are performed, the instruments are detached from the rope and a next rope may be inspected. Accordingly, the typical checking of the condition takes time and requires highly qualified experts that are specialized in maintenance of the ropes. The availability of the experts and the measurement instruments to check the ropes of the cranes may also affect the scheduling of the rope maintenance, making the scheduling of the maintenance even more difficult, whereby high operational efficiency is even more difficult to achieve.

Accordingly, condition of the ropes is typically checked manually by instruments that are temporarily installed to the ropes by the service personnel. Typically these instruments check the condition of the rope by magnetically saturating the rope and measuring the magnetic flux inside and outside of the rope. These instruments fit tightly around the monitored rope to allow efficient transfer of the magnetic flux to and from the rope. However, the instruments have to be removed after the measurements have been performed so that the ropes and the crane may be operated for handling payload. If these instruments are not removed from the ropes, the instruments may travel attached to the rope to hoisting machinery and consequently result in seriously damaging the hoisting machinery and even dropping any payload carried by the ropes to the ground.

Consequently, the present instruments require manual work by maintenance personnel which introduces the possibility of human error and on the other hand since the present instruments cannot be used when the payload is being handled, monitoring the condition of the ropes requires scheduling of maintenance during which the crane is not used for handling payload.

US RE40166E discloses a magnetic non-destructive method and apparatus for measurement of cross sectional area and detection of local flaws in ropes. A magnetic flux is created to the rope under test. A base flux flows through the rope between the poles. Some of the magnetic flux is leaked outside of the rope and forms a leakage flux. Accessory inserts are used to enable testing of ropes having various diameters within a predetermined range.

Accessory inserts should fit tightly between the poles and the rope for efficiently conveying the magnetic flux between the rope and the poles and thereby avoiding losses in the magnetic flux. Thereby, the accessory inserts are specific to each rope diameter used.

Ropes exist in various sizes depending on their application area. The cross-sectional diameter of the rope may vary for example due to the construction of the rope, manufacturing material, required strength and requirements posed by the application area of the rope. On the other hand the diameter of the rope may change during its use, for example due to wearing of the rope.

The distance of the poles from the rope under test is changed as the diameter of the rope is changed. The distance of the poles to the rope affects the proportion of the magnetic flux that is leaked outside of the rope and the proportion of the magnetic flux that is carried through the rope. This causes inaccuracies to the testing of the rope by measuring the magnetic flux. Accordingly, the distance of the poles to the rope affects the magnetization of the rope under test, i.e. the amount of magnetic flux through the rope under test. The magnetic flux sees air gaps between poles and the rope under test as resistances, whereby an increase of the air gaps is reflected to a decrease in the amount of magnetic flux that is carried by the rope. As the amount of magnetic flux carried by the rope is decreased by the increased air gaps, the saturation of the rope is also decreased and the saturation of the rope may even be removed. The lower saturation of the rope may cause that defects in the rope are not detected since the low saturation of the rope provides that the proportion of the magnetic flux carried by the rope and leaking outside the rope due to defects is reduced or even negligible, making it difficult or even impossible to detect defects in the rope from the magnetic flux leaking outside of the rope.

On the other hand, if the variance of the rope diameter is compensated by inserts between the poles and the rope under test, the fitting of the inserts takes time which reduces the operational efficiency of the ropes and the crane where the ropes are installed. Moreover, installation of the inserts requires competent personnel at least for the sake of performing the installation securely in locations that may be high above the ground and/or have a danger of high voltage. These personnel may not be available in the same country or even in the same continent. Thereby the use of the ropes may be prevented at least for the sake of security aspects until the competent personnel are on-site to perform the installation. The manual work needed for installing the inserts also introduces a risk of human error. Moreover, attachment of parts such as the inserts that are installed such that they may be later uninstalled, are prone to loosen up unintentionally which introduced the risk of the loosening being undetected and false test results of the rope and an increased need of maintenance.

SUMMARY

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

Various embodiments of the invention comprise an apparatus, a monitoring arrangement, a method and a crane as defined in the independent claims. Further embodiments of the invention are disclosed in the dependent claims.

According to an aspect there is provided an apparatus for monitoring a condition of an elongated ferrous object having a longitudinal axis, said apparatus including at least one magnetizing circuit including magnetic poles separated along the longitudinal axis, and magnetic field sensors arranged at the poles, said poles comprising pole shoes for directing magnetic flux between the poles and the monitored object, the pole shoes comprise openings between the monitored object and the poles, an opening comprising two ends separated in a direction perpendicular to the longitudinal axis by a mid-section defining a smaller opening than the ends for concentrating the magnetic flux at the mid-section.

According to an aspect there is provided an arrangement comprising one or more elongated objects for hoisting payload and an apparatus according to an aspect attached to the elongated objects.

Some of the embodiments provide improvements in monitoring elongated ferrous objects by concentrating a magnetic flux through the monitored object, so that a larger gap between the monitored object and the magnetic poles may be allowed. Preferably magnetic field sensors are positioned to the concentrated magnetic flux. In this way, the magnetic field sensors are provided a substantially homogenous and strong magnetic flux for accurate measurement of the magnetic flux. An accurate measurement of the magnetic flux may provide for a reliable forecasting of lifespan of ropes.

Some embodiments provide improvements in measuring the magnetic field outside a saturated monitored object.

Further improvements become apparent from the accompanying description.

BRIEF DESCRIPTION OF THE DRAWINGS

In the following embodiments are described with reference to the accompanying drawings in which:

FIG. 1 illustrates a general architecture of arrangement for monitoring elongated ferrous objects having a longitudinal axis according to an embodiment;

FIG. 2a illustrates monitoring a condition of a longitudinal ferrous object having a longitudinal axis by an apparatus comprising magnetizing circuits, according to an embodiment;

FIG. 2b illustrates a side-view and a flow of magnetic flux between poles of one of the magnetizing circuits of FIG. 2a;

DETAILED DESCRIPTION

Figure 3:
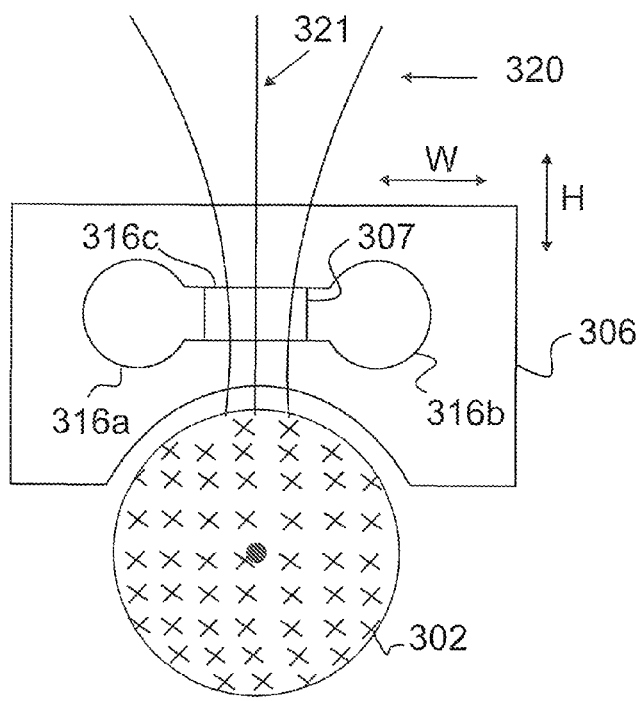
FIG. 3 illustrates a cross-sectional view of a pole shoe of a magnetizing circuit according to an embodiment.

In the following elongated ferrous objects are referred to as ropes made of iron or derived from iron. The presence of iron gives magnetic properties to the ropes such that the rope may be magnetised. Magnetic properties may be provided by using a ferrous material for the rope. Ferrous materials include ferrous metals such as mild steel, carbon steel, cast iron, and wrought iron. Most ferrous metals have magnetic properties, for example provided by the use of ferrite ($\alpha$-Fe) in the metal alloy.

In various embodiments payload may refer to movable objects that are transported between physical locations on the ground, in buildings and/or in vehicles. The movable objects may be cargo transported by vehicles between an origin, for example a harbour, and a destination, for example a warehouse. In one example, the movable objects may be containers that have standardized dimensions and are conventional in transportation of goods by ships and trucks.

Examples of the elongated ferrous objects include but are not limited to objects such as a steel rod, tube, wire or wire rope. For purposes of description the term "rope" is used to refer to all of these structures. It is understood that the cross section of the rope can define a circular, curvilinear, rectangular, triangular, or faceted profile.

A typical rope is a linear collection of plies, yarns or strands which are wound together in order to combine them into a larger and stronger form. Materials suitable for the ropes include but are not limited to steel and pig iron (with a carbon content of a few percentage) and alloys of iron with other metals. Also other materials may be used provided they can be magnetized to allow a flow of magnetic flux within the material. Also requirements regarding the practical implementations of the ropes should be considered, such as the strain the ropes have to endure.

FIG. 1 illustrates a general architecture of monitoring arrangement of ropes according to an embodiment. The rope monitoring arrangement includes one or more apparatuses 106 for monitoring a condition of the ropes. The apparatuses have magnetizing circuits that generate a magnetic flux between magnetic poles. The apparatuses are installed to the ropes such that the rope may be subjected to the generated magnetic flux and the rope is saturated by the magnetic flux. Consequently, the rope is saturated along its length between the poles. The generated magnetic flux flows between the poles through the rope. The apparatuses include sensors that may measure the magnetic flux entering and/or leaving the rope. Also other sensors may be provided as is illustrated in FIG. 2b.

Referring back to FIG. 1, the ropes may be attached to a supporting structure 102, whereby payload and payload handling equipment 104, for example hooks, may be attached to the ropes to be supported by the ropes so that the payload may be handled, e.g. hoisted or lowered by the rope. The ropes may be attached to the supporting structure such that they are movable, for example by hoisting. Hoisting machinery may be used to provide the hoisting by installing the ropes to the hoisting machinery.

A controller 108 may be connected to the apparatuses installed to the ropes. The controller may be directly connected to the apparatuses or connected via the supporting structure. A direct connection between the controller and apparatus may be an electrical connection implemented for example by a data bus for example Industry Standard Architecture (ISA) or Peripheral Component Interconnect (PCI) bus used in computers, when the controller is implemented within the apparatuses. The controller may be a computer or a processing unit including logic circuitry and memory, for example. In one example, the controller may be a Programmable Logic Controller PLC as is conventional in cranes. In cranes, the PLC connects to the crane functions, for example the hoisting machinery. An industrial bus, for example Profibus (Process Field Bus) and CANopen, may be used for connecting the PLC and the crane functions. The memory may be a volatile or a non-volatile memory, for example EEPROM, ROM, PROM, RAM, DRAM, SRAM, firmware, programmable logic, etc.

Accordingly, in one example the apparatuses installed to the ropes may be connected to the controller via a connection to an industrial bus provided at the supporting structure. The connection between the apparatuses installed to the ropes and the supporting structure may be provided by a wireless or wired connection (not shown). A wireless connection may be provided by information communicated on a radio frequency band by a transmitter and a receiver employing corresponding protocols that allow the transfer of the information between them. In one example a wireless connection may be implemented by a Wireless Local Area Network connection according to the IEEE 802.11 family of specifications.

A wired connection may be implemented by electrical wiring that connects to the industrial bus in the supporting structure via an adaptor. The electrical wiring and communications protocols may be implementation specific. In one example, the electrical wiring may be implemented as an industrial bus connection.

The apparatuses installed to the ropes may operate at least as transmitters to allow transfer of measurement information to a receiver located at the supporting structure. However, it is possible that the connection between the supporting structure and the apparatuses installed to the ropes is bidirectional and both ends of the connection operate as transmitters and receivers, i.e. transceivers.

Accordingly, in one example, a wired connection provided by an industrial bus may be used between the supporting structure, e.g. the hoisting machinery, and the controller, and a wireless connection may be used between the supporting structure and a monitoring apparatus attached to the ropes.

The controller may connect to a service centre 112 over a network 110. The network may be a wide area network including one or more access networks that may provide wired or wireless access to the network. The wireless access networks may be implemented by the WLAN or by mobile communications networks defined by the 3$^{rd}$ Generation Partnership Project, for example, Global System for Mobile Communications, Terrestrial Trunked Radio Access, Universal Mobile Telecommunications System, Long Term Evolution and LTE-Advanced. Wired access may be provided over Ethernet connections. Internet Protocol version 4 or 6 may be used in addressing in the communications.

The controller and the service centre may be equipped with adapters that provide the communications capabilities on the connections. In one example, the adapters for wireless communications include modems that operate according to the above-mentioned communications standards. Adapters for wired connections may include bus cards connect to internal buses and thereby provide wired connectivity to hardware and/or software platforms of the described entities.

The service centre may be connected to a data storage 114 that stores information of installed ropes. The stored information may comprise information identifying the ropes and include information on condition of the ropes. The ropes may be identified by the crane and/or crane functionality they are installed to, for example. The condition may be specified as a time period until maintenance is to be performed and/or as a level of the condition. Different condition levels may be: excellent, good, needs maintenance and damaged. Each level may be specified by one or more thresholds for determining which condition matches the measurements received from the rope. The controller may process the measurement information from the ropes and determine the condition and/or the time period until maintenance should be performed. It is also possible that the service centre receives the measurement information from the ropes via the controller and the service centre determines the condition and/or the time period until maintenance should be performed. The data storage may be internal to the service centre or external to the service centre. The service center may be implemented as a computer including an internal bus that connects to the data storage via the bus. In another example the data storage resides in a server external to the service centre and the data storage may be connected over a wired or wireless connection that may be implemented according to the communications standards described above.

Preferably the apparatuses installed to the ropes allow movement of the ropes as they are hoisted. In one example the apparatus in installed around a rope that is monitored by the apparatus. Accordingly, as the rope is hoisted, it moves through the apparatus installed around the rope. In this way the apparatus may measure the rope through the whole length of the rope as the rope is hoisted. To allow the movement, the apparatus has a passage that allows movement of the rope in the hoisting direction. In a typical deployment scenario, where the ropes are hoisted in a vertical direction, for example in lifting payload or lowering payload to the ground, the apparatuses installed to the ropes may be supported to the supporting structure by cabling to suspend them at a suitable position with respect to the rope. This may be desirable for practical reasons to keep the apparatus from sliding to the hook, for example. On the other hand it is possible that the apparatus is integrated to the hook or other structure, where the rope is passed through, and no cabling is needed to support the apparatus. However, whether support is needed or not and how the support is implemented relates to details that need not to be discussed herein to avoid obscuring the description with too much details.

FIG. 2a illustrates monitoring a condition of a rope 202 by an apparatus 200 comprising magnetizing circuits according to an embodiment. The magnetizing circuits are illustrated in their closed position around the rope. In the closed position the magnetizing circuits form a passage for the rope to travel between the magnetizing circuits. Accordingly, the diameter of the passage is larger than the diameter of the rope. The apparatus may be used to implement an apparatus installed around the ropes described in a rope monitoring arrangement of FIG. 1. In FIG. 2a, two magnetizing circuits are arranged around the rope. Each of the magnetizing circuits includes two poles 204a, 204b that are arranged along the longitudinal axis of the rope. The poles magnetically saturate the rope, whereby a magnetic flux flows in the rope, along the length of the rope, between the poles of both magnetizing circuits. The magnetic poles may be provided by permanent magnets or by electromagnets, such that a magnetic flux is generated, as is well-known to a skilled person and therefore, this does not need to be discussed further herein.

The poles of each magnetizing circuit are connected by magnetic flux guides 208a, 208b that guide the magnetic flux between the poles. Accordingly, the magnetic flux guides guide the magnetic flux between the poles outside the rope. FIG. 2b illustrates a side-view and an exemplary flow path 211 of the magnetic flux between poles of one of the magnetizing circuits of FIG. 2a. Preferably the magnetic flux introduced by both magnetizing circuits to the rope is substantially the same.

Pole shoes 206a, 206b are arranged between the poles and the rope. The pole shoes guide the magnetic flux between each of the poles and the rope. In this way the magnetic flux leaving the poles may be concentrated to the rope as well as the magnetic flux leaving the rope may be concentrated to the poles.

The magnetizing circuits are arranged on opposite sides of the rope. The pole shoes are arranged at a distance from the rope such that the magnetic flux may flow between the rope and each of the pole shoes. Accordingly, the pole shoes define a passage for the rope as the rope moves through the magnetizing circuits. Preferably the pole shoes are designed to a constant distance from the rope, thereby following the shape of the rope passing the magnetizing circuits. Accordingly, the cross section of the apparatus, when the magnetizing circuits are closed around the rope, matches substantially the cross-section of the rope, at the side of the magnetizing circuits that meet the rope.

The magnetizing circuits arranged around the rope may be the same and made of a ferrous material. The magnetizing circuits may be implemented in opposite halves of a structure, for example in pieces of alloy bodies or any non-ferrous material that house the magnetizing circuits. It is also possible to implement the magnetizing circuits without a separate housing structure, whereby the air surrounding the magnetizing circuits may serve the purpose of the housing by magnetically isolating the magnetizing circuits.

The magnetizing circuits may include one or more sensors 207a, 207b, 209 for measuring the magnetic flux. The sensors may be installed to each of the poles to measure the magnetic flux leaving one pole towards the rope and to measure the magnetic flux received at the other pole from the rope. In this way the magnetization of the rope may be measured. The measured magnetization of the rope may be used to determine the condition of the rope. Variations of the magnetization may indicate a faulty rope, one or more foreign objects being attached to the rope and/or a fault in the measurement equipment. The faulty rope may comprise a rope with increased diameter and/or a decreased diameter as described above. It may also be possible to detect faulty ropes even if their diameter is not reduced or increased.

One or more sensors 209 may be installed between the poles in the longitudinal direction of the rope. The longitudinal direction may be defined by the longitudinal axis of the rope. Preferably the sensors are installed parallel to the rope in the longitudinal direction. In this way the magnetic flux may be measured that has leaked outside the rope. This may happen, when the rope is faulty.

The magnetic flux may be measured by its magnitude. The magnitude may be indicated by analogue or digital signals. The signals may be electrical signals that have voltages that correspond to the measured magnitudes of the magnetic flux.

FIG. 3 illustrates a cross-sectional view of a pole shoe 306 of a magnetizing circuit according to an embodiment. The pole shoe comprises openings between the rope 302 and a magnetic pole. The openings 316a, 316b are located away from a direct path 321 of the magnetic flux 320 between the pole and a center of the rope illustrated by a black dot. The magnetic pole shoe may be the magnetic pole shoe illustrated in FIG. 2a or 2b, for example. The shape of the pole shoes and the strength of the magnetic poles are preferably designed such that the rope is saturated, when the magnetizing circuit is around the rope and a magnetic flux is generated to the rope by the magnetizing circuit. In FIG. 3, the openings are provided by a single opening 316a, 316b, 316c that has two ends 316a, 316b, separated in a direction W perpendicular to the longitudinal direction of the rope by a mid-section 316c. The openings provide that the magnetic flux between the pole and the rope may be concentrated and is substantially homogeneous at the point of measurement, whereby a larger gap may be allowed between the rope and the pole shoes without losing the measurement accuracy. The larger gap provides that the magnetizing circuits allow movement of the monitored rope, whereby the magnetizing circuits may be attached around the rope during the operational use of the rope, e.g. payload handling. Moreover, since the openings provide efficient flow of the magnetic flux between the rope and the poles, reliable monitoring of the ropes that have a reduced diameter, for example due to wearing, is facilitated.

The mid-section defines a smaller opening than the ends, whereby the magnetic flux that is guided through the pole shoe has a greater magnetic resistance to travel through the openings at the ends than through the mid-section. Preferably the opening defined by the mid-section is smaller at least in the height H direction. In this way the magnetic flux is concentrated and substantially homogenous at the mid-section and the magnetic flux density is greater at the mid-section than in the openings around the mid-section. It should be appreciated that the magnetic flux through the pole shoe may also travel around the openings, while still travelling within the pole shoe. In this way it may be provided that the magnetic flux travels between the poles and the rope also at the sides of the rope, where the pole shoe is covering the rope. The exact position and size of the openings may be designed to avoid leakage of the magnetic flux from the pole shoe, while allowing the magnetic flux to travel between the pole and the rope.

The mid-section comprises a magnetic flux sensor 307 that measures the magnetic flux passing between the pole and the rope. The resulting magnetic flow measured in the middle of the mid-section is substantially homogeneous. Consequently, the magnetic flow entering and leaving the rope may be measured accurately. The mid-section is preferably located directly between the rope and the pole. The position of the mid-section in the cross-section of FIG. 3 may be defined to be centered in its width direction W to the direct path of the magnetic flux between the pole and the center of the rope. The width direction may be perpendicular to the height H direction. The illustrated cross-sections of the openings may have various shapes, for example circular or oval shapes. It should be appreciated that the illustrated openings in the cross-sectional view extend in practise along the length of the rope in the pole shoe.

The mid-section of the openings is preferably wide enough to accommodate the sensor. In the height direction H, i.e. in the direction of the direct path of the magnetic flux, the mid-section preferably defines a smaller opening by being lower than the ends. The mid-section is further positioned symmetrically with respect to the ends of the opening such that the mid-section is centered to the ends in the height direction. In this way the, magnetic flux entering and leaving the mid-section is guided by the ends that are shown as resistances to the magnetic flux. It should be appreciated the ends have preferably a lower permeability than the surrounding pole shoe to facilitate the guiding of the magnetic flux. Accordingly, in one example the pole shoe is of ferrous material and the opening may be air or any other material that has a low permeability compared to the pole shoe.

The magnetic flux is illustrated in the FIG. 3 by flux lines 320 that enter the rope through the pole shoe and enter the rope, where the magnetic flux propagates away from the viewer as notated by crosses as is conventional indicating direction of the magnetic flux. In the illustration, the rope is saturated by the magnetic flux to monitor the rope by measuring the magnetic flux carried by the rope and the magnetic flux leaking outside the saturated rope. The magnetic flux carried by the rope may be measured by sensors at the pole shoes according to FIG. 2b. The magnetic flux leaking out of the saturated rope may be measured by the sensor between the poles and next to the monitored rope as illustrated in FIG. 4.

Referring to FIG. 3, the openings in the pole shoes provide concentrating the magnetic flux to the magnetic field sensor and to the monitored rope. In this way the magnetic field that the monitored rope is subjected to, may be accurately measured. The pole shoe of FIG. 3 may be installed to poles of the magnetizing circuit of FIGS. 2a and 2b. In this way the rope may be saturated by the magnetizing circuits such that the magnetic flow is concentrated to the sensors in the pole shoes. FIG. 4 illustrates positioning of a magnetic field sensor 409 between magnetic poles 406 of magnetizing circuit and next to the monitored rope 402 of a monitoring apparatus according to an embodiment. The magnetic poles may include pole shoes as described in FIG. 3. The magnetizing circuits may be according to FIG. 2a or 2b. The magnetic field sensor comprises a sensor element 419 for measuring magnetic flux. The sensor element may have a direction of sensitivity, where the magnetic flux 420 may be efficiently received. The magnetic field sensor is positioned between the poles next to the rope such that the sensor element has its direction of sensitivity directed parallel to the longitudinal axis of the rope being monitored. A block 429 of ferrite, for example a ferrite bead, is arranged between the magnetic field sensor and at least one of the magnetic poles. Ferrite beads are typically used in electronics, for example in Electromagnetic Compatibility (EMC) and Radio Frequency Interference (RFI) protection. The block of ferrite concentrates the magnetic flux outside the monitored rope to the magnetic field sensor. In this way the magnetic field outside of the rope and between the poles may be accurately measured. On the other hand, it provides a greater gap to the monitored rope by improved efficiency in directing the magnetic flux through the magnetic field sensor, which again facilitates higher signal amplitudes in the sensor.

Since the ferrite bead is of strongly ferromagnetic material, it operates as a "lens" to the magnetic flux, by collecting the magnetic flux from the rope to a target location. The sensor element is preferably positioned to the target location or at least close to the target location for efficient measurement of the magnetic flux. The sensor element 409 and the block of ferrite may be arranged on a circuit board 439. The circuit board positions the block of ferrite and the magnetic field sensor with respect to each other such that the magnetic flux is guided by the block of ferrite to the direction of sensitivity of the magnetic field sensor. The circuit board provides also electrical connections to the sensor such that the measurements of the magnetic field may be communicated to be further processed, for example by a computer or other processing means that typically comprise a processor and a memory that is electrically interconnected.

Figure 4:
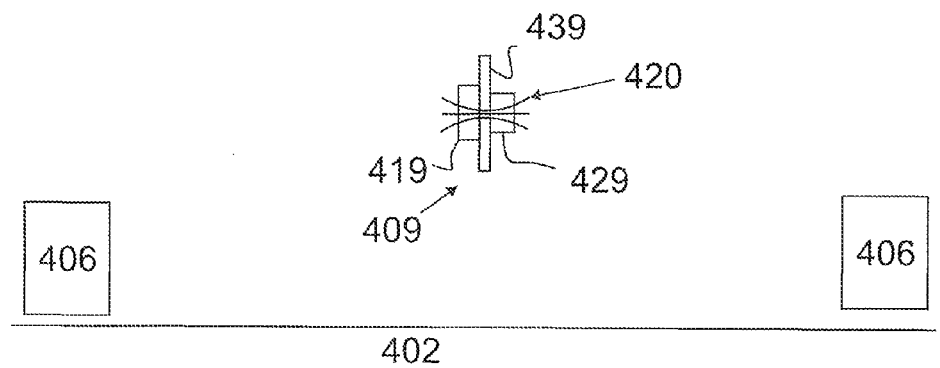
FIG. 4 illustrates positioning of a magnetic field sensor between magnetic poles of magnetizing circuit and next to the monitored longitudinal object of a monitoring apparatus according to an embodiment.

The magnetic field sensor of FIG. 4 may be installed to the magnetizing circuit of FIGS. 2a and 2b or a body housing the magnetizing circuits. A faulty rope causes a decrease of the magnetic flux within the rope, when the rope is magnetized by the magnetizing circuit. The magnetic field outside the rope is correspondingly increased and the field may be measured by the magnetic field sensor positioned between the poles. The block of ferrite concentrates the magnetic field outside the rope to the magnetic field sensor for accurate measurement of the magnetic field outside the rope.

Figure 5:
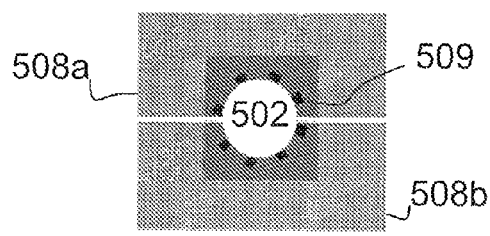
FIG. 5 illustrates a cross-section between the poles of the magnetizing circuits in the direction of the rope entering the passage formed by the magnetizing circuits.

FIG. 5 illustrates a cross-section between the poles of the magnetizing circuits in the direction of the rope 502 entering a passage formed by the magnetizing circuits 508a, 508b. In the illustrated cross-section, the sensors are arranged at the same level in the longitudinal direction of the rope. The apparatus comprises a plurality of magnetic field sensors 509 positioned between the poles and around a perimeter of the monitored rope. The magnetic field sensors may be positioned between the magnetic poles according to the illustration in FIG. 4. FIGS. 2a and 2b illustrate examples of magnetizing circuits of FIG. 5. In FIG. 5 the magnetizing circuits are around the rope similar to the magnetizing circuits of FIG. 2a.

It should be appreciated that the plurality of magnetic field sensors around the perimeter of the rope may be positioned at least partly at different positions along the length of the monitored object. Accordingly, the sensors may be interleaved around the perimeter in the direction of the length of the monitored object such that they are partly parallel with each other. It is possible for example that the odd sensors are substantially parallel only with other odd sensors, and even sensors are substantially parallel only with other even sensors. It is also possible that all the plurality of magnetic field sensors are all at different positions. The different positions may be provided for example by arranging the sensors around the perimeter into a form of a circular helix. The use of different positions facilitates positioning the magnetic field sensors around the rope even, when there is not much space to be used for the sensors around the perimeter of the rope, for example when ropes having small diameters are measured. Correspondingly, also it is possible to position the sensors to a specific nominal distance of the rope such that faults in the monitored rope may be examined from different angles. In such a case, positions of the sensors and measurement angles are known in advance by the arrangement of the sensors around the rope, for example by the arrangement of the sensors in the magnetizing circuits or in the bodies housing the magnetizing circuits around the rope. The signal processing takes care of handshaking and correspondence of the measured signals from the sensors, when the fault is in the position of each sensor. In this way the fault may be examined from different directions and the accuracy of determining the severity of the fault may be improved.

In an embodiment, referring now to FIG. 1 and FIG. 5, the supporting structure 102 and/or controller 108 can provide information of velocity of the moving rope. Once mechanical distances of sensors 509 and angular positions around the rope are known, it is possible to connect detected signals of multiple sensors on a timeline and then point out each fault and its signals from various angles around the rope.

It will be obvious to a person skilled in the art that, as the technology advances, the inventive concept can be implemented in various ways. The invention and its embodiments are not limited to the examples described above but may vary within the scope of the claims.

The invention claimed is:

1. An apparatus for monitoring a condition of an elongated ferrous object having a longitudinal axis, said apparatus including at least one magnetizing circuit including magnetic poles separated along the longitudinal axis, and magnetic field sensors arranged at the poles, said poles comprising pole shoes for directing magnetic flux between the poles and the monitored object, wherein the pole shoes comprise openings between the monitored object and the poles, an opening comprising two ends separated in a direction perpendicular to the longitudinal axis by a mid-section defining a smaller opening than the ends for concentrating the magnetic flux at the mid-section.

2. The apparatus according to claim 1, wherein the magnetic field sensors are arranged to the mid-section in each pole shoe.

3. The apparatus according to claim 1, whereby the condition of the object is monitored by measuring the magnetic flux through the pole shoes.

4. The apparatus according to claim 1, further comprising: at least one magnetic field sensor positioned between the poles next to the elongated ferrous object, said at least one magnetic field sensor having a direction of sensitivity directed parallel to the longitudinal axis.

5. The apparatus according to claim 1, further comprising: at least one magnetic field sensor positioned between the poles next to the elongated ferrous object, said at least one magnetic field sensor having a direction of sensitivity directed parallel to the longitudinal axis and a block of ferrite arranged between the magnetic field sensor and at least one of the magnetic poles.

6. The apparatus according to claim 5, wherein a magnetic flux outside of the elongated ferrous object is collected by the ferrite block to a target location, and the at least one magnetic field sensor is positioned to the target location or at least close to the target location.

7. The apparatus according to claim 1, further comprising a plurality of magnetic field sensors positioned between the poles, around the perimeter of the monitored elongated ferrous object.

8. The apparatus according to claim 1, wherein the mid-section is lower than the ends in the direction of the direct path of the magnetic flux between the pole and the monitored elongated ferrous object and the mid-section is positioned symmetrically with respect to the ends of the opening such that the mid-section is centered to the ends in the direction of the direct path of the magnetic flux between the pole and the monitored elongated ferrous object.

9. The apparatus according to claim 1, wherein the elongated ferrous object comprises a rope of a hoisting machinery, including a hoisting machinery in a crane, a ropeway, an elevator, a conveyor in a mine shaft or a ski lift.

10. An arrangement comprising one or more elongated objects for hoisting payload and an apparatus for monitoring a condition of an elongated ferrous object having a longitudinal axis, said apparatus including at least one magnetizing circuit including magnetic poles separated along the longitudinal axis, and magnetic field sensors arranged at the poles, said poles comprising pole shoes for directing magnetic flux between the poles and the monitored object, wherein the pole shoes comprise openings between the monitored object and the poles, an opening comprising two ends separated in a direction perpendicular to the longitudinal axis by a mid-section defining a smaller opening than the ends for concentrating the magnetic flux at the mid-section, wherein the apparatus is attached to the elongated objects, when payload is handled by the elongated ferrous objects.

11. The arrangement according to claim 10, further comprising a hoisting machinery in a crane, including a gantry crane or a bridge crane, a ropeway, an elevator, a conveyor in a mine shaft or a ski lift.

* * * * *